(12) United States Patent
Chavan et al.

(10) Patent No.: US 9,409,855 B2
(45) Date of Patent: Aug. 9, 2016

(54) ASYMMETRIC SYNTHESIS OF (−)-VENLAFAXINE USING ORGANOCATALYST

(71) Applicant: COUNCIL OF SCIENTIFIC & INDUSTRIAL RESEARCH, New Delhi (IN)

(72) Inventors: Subhash Prataprao Chavan, Maharashtra (IN); Sumanta Garai, Maharashtra (IN); Kailash Pralhad Pawar, Maharashtra (IN)

(73) Assignee: COUNCIL OF SCIENTIFIC & INDUSTRIAL RESEARCH (IN)

( * ) Notice: Subject to any disclaimer, the term of this patent is extended or adjusted under 35 U.S.C. 154(b) by 10 days.

(21) Appl. No.: 14/416,649

(22) PCT Filed: Jul. 25, 2013

(86) PCT No.: PCT/IN2013/000464
§ 371 (c)(1),
(2) Date: Jan. 23, 2015

(87) PCT Pub. No.: WO2014/016852
PCT Pub. Date: Jan. 30, 2014

(65) Prior Publication Data
US 2015/0175524 A1 Jun. 25, 2015

(30) Foreign Application Priority Data

Jul. 25, 2012 (IN) ............................ 2300/DEL/2012

(51) Int. Cl.
*C07C 213/02* (2006.01)
*C07C 213/00* (2006.01)

(52) U.S. Cl.
CPC .............. *C07C 213/02* (2013.01); *C07C 213/00* (2013.01); *C07C 2101/14* (2013.01); *C07C 2101/16* (2013.01)

(58) Field of Classification Search
CPC ..................................................... C07C 213/02
See application file for complete search history.

(56) References Cited

PUBLICATIONS

Pansare et al. J. Am. Chem. Soc. 2006, 128, 9624-9625.*
International Search Report and the Written Opinion of the International Searching Authority, PCT/IN2013/000464, Council of Scientific & Industrial Research, Nov. 7, 2013.
Chavan, Subhash P. et al., Asymmetric total synthesis of (−)-venlafaxine using an organocatalyst, Tetrahedron Letters 54 (2013) pp. 2137-2139.
Bhuniya, Rajib et al., Asymmetric synthesis of both the enantiomers of antidepressant venlafaxine and its analogues, Tetrahedron Letters 53 (2012) pp. 1990-1992.

* cited by examiner

*Primary Examiner* — Clinton Brooks
(74) *Attorney, Agent, or Firm* — McDonald Hopkins LLC

(57) ABSTRACT

The patent discloses an asymmetric synthesis of (−)-venlafaxine using an organocatalyst via a unified strategy employing organcatalytic Michael addition, regio-selective dehydration and selective epoxide ring opening.

4 Claims, 4 Drawing Sheets

Chromatogram for racemic venlafaxine

Chromatogram for optically pure venlafaxine

Scheme 1: Retrosynthetic analysis of (-)-venlafaxine

Scheme 2: Synthesis of venlafaxine

ASYMMETRIC SYNTHESIS OF (−)-VENLAFAXINE USING ORGANOCATALYST

TECHNICAL FIELD OF INVENTION

The invention relates to the asymmetric synthesis of (−)-venlafaxine using an organo catalyst. Particularly, the invention relates to the selective synthesis of one enantiomer of venlafaxine using the organocatalyst.

BACKGROUND AND PRIOR ART

Venlafaxine is a new generation antidepression drug, first introduced in 1993. It is used for the treatment of major depressive disorder (MDD), as a treatment for generalized anxiety disorder, and co-morbid indications in certain anxiety disorders with depression. In 2007, venlafaxine was the sixth most commonly prescribed antidepressant on the U.S. retail market, with 17.2 million prescriptions. Although venlafaxine is sold as a racemate, (−)-venlafaxine is a more potent inhibitor of norepinephrine synaptosomal uptake while (+)-venlafaxine is more selective in serotonin uptake. It is different from other antidepressants in that it has no or little activity on a variety of neuroreceptors. (e.g. α OR β-adrenergic receptors, muscarinic receptors, cholinergic receptors, histaminic receptors etc.).

There are number of racemic syntheses reported for venlafaxine, including those by the inventors. These synthetic routes for racemic venlafaxine mainly involve the condensation of cyclohexanones with 4-methoxyphenyl acetic acids or 4-methoxyphenyl acetonitriles followed by functional group manipulation.

As both enantiomers possess different biological activities, therefore asymmetric synthesis of Venlafaxine is a subject matter of interest.

Nanda et al in Tetrahedron Letters 53 (2012) 1990-1992 reported an enzyme based resolution for asymmetric synthesis of venlafaxine. Their strategy included (S)-HNL catalyzed synthesis of cyanohydrins from cyclic ketones and lipase-PS catalyzed kinetic resolution for creation of the stereocenter.

Chem. Commun., 2006, 3110-3112 disclose β-Amino esters which are readily formed from rhodium(II) prolinate-catalyzed intermolecular C—H insertion between methyl aryldiazoacetates and a bis-silyl protected methylamine. This was applied for effective synthesis of venlafaxine with enantiomers obtained with moderate yields moderate % ee.

But prior art methods suffer from the main drawback of having to resolve the enantiomers in a separate dedicated step, and yet result in only moderate yield. Also, these processes employ hazardous and potentially explosive reagents. They need dry, inert conditions during use of Grignard's reagent and many processes need cryogenic conditions. Also, these prior art processes use metal based catalyst which are not environmentally friendly.

OBJECTS OF INVENTION

The main object of the invention is to provide a process for asymmetric synthesis of (−)-venlafaxine, wherein one enantiomer is obtained in high enantiomeric purity.

Another object of the invention is to provide a process to those results selectively in one enantiomer of venlafaxine, without the need for a step of resolution.

SUMMARY OF INVENTION

Accordingly, the present invention provides a process for asymmetric synthesis of enantiomerically pure venlafaxine with ee≥99% comprising the steps of:

a. reacting anisaldehyde with nitromethane in mole ratio 1:11.8 in presence of ammonium acetate in acetic acid under sonication condition at room temperature ranging between 25-35° C. for a period ranging between 2-4 hrs to obtain nitro styrene;
b. michael addition of nitrostyrene as obtained in step (a) with cyclohexanone in mole ratio 1:5 in presence of proline based organocatalyst under stirring at room temperature ranging between 25-35° C. for a period ranging between 23-25 hrs in the presence of p-toluene sulphonic acid to obtain nitro ketone;
c. reducing nitro ketone of step (b) using $NaBH_4$ in THF: H2O (9:1) to obtain crude alcohol (2S)-2-((R)-1-(4-methoxyphenyl)-2-nitroethyl)cyclohexan-1-ol which on subjecting to nitro reduction by $NiCl_2.6H_2O$ and sodium borohydride in MeOH as a solvent, afforded the resultant amine (2S)-2-((R)-2-amino-1-(4-methoxyphenyl)ethyl)cyclohexan-1-ol which on in situ protection by benzylchloroformate in presence of $Et_3N$ as a base furnished Cbz protected amino alcohol benzyl ((2R)-2-((1S)-2-hydroxycyclohexyl)-2-(4-methoxyphenyl)ethyl)carbamate;
d. treating amino alcohol of step (c) with mesyl chloride in presence of $Et_3N$ as a base in DCM solvent under reflux condition at temperature ranging between 40-45° C. for a period ranging 14-25 hrs to give the crude mesylated reaction mixture which further on treatment with DBU in acetonitrile solvent furnished selectively more substituted double bond product benzyl (R)-(2-(cyclohex-1-en-1-yl)-2-(4-methoxyphenyl)ethyl)carbamate;
e. subjecting compound (R)-(2-(cyclohex-1-en-1-yl)-2-(4-methoxyphenyl)ethyl)carbamate of step (d) with NaH and MeI in dry THF to obtain benzyl (R)-(2-(cyclohex-1-en-1-yl)-2-(4-methoxyphenyl)ethyl)(methyl)carbamate;
f. epoxidation of benzyl (R)-(2-cyclohex-1-en-1-yl)-2-(4-methoxyphenyl)ethyl)(methyl)carbamate of step (e) by treating with m-CPBA in presence of $NaHCO_3$ in DCM under stirring at temperature ranging between 25-35° C. for a period ranging between 1-3 hrs to afford crude epoxide benzyl ((2R)-2-(7-oxabicyclo[4.1.0]heptan-1-yl)-2-(4-methoxyphenyl)ethyl)(methyl)carbamate;
g. subjecting the crude epoxide of step (f) to selective epoxide opening as well as carbamate reduction in one pot using lithium aluminum hydride at reflux condition at temperature ranging between 65-70° C. for a period ranging 4-5 hrs in THF to afford (−)-venlafaxine.

In one embodiment of the present invention the overall yield of enantiomerically pure (−)-venlafaxine is in the range of 21-22%.

In an embodiment of the present invention the enantioselectivity of (−)-venlafaxine is in the range of 99-99.9%.

In another embodiment of the present invention proline based organocatalyst used in step (b) is (S)—N1,N1-dimethyl-N2-(pyrrolidin-2-ylmethyl)ethane-1,2-diamine

DETAILED DESCRIPTION OF INVENTION

Figure 1:
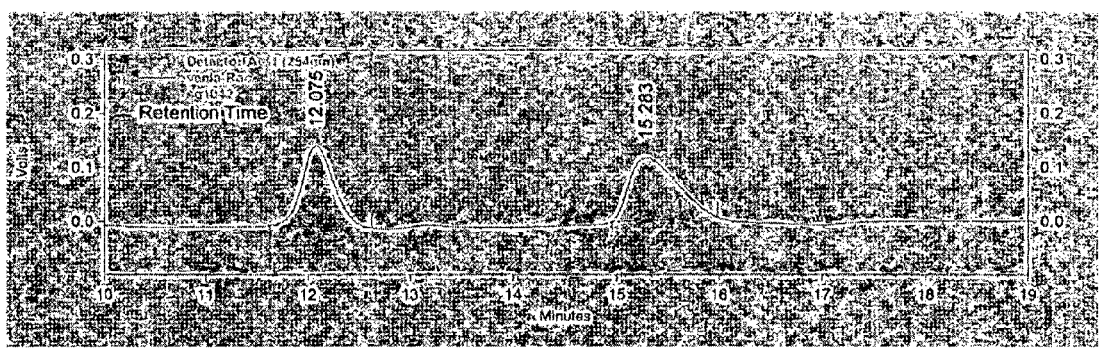
FIG. 1: Chromatogram for racemic venlafaxine
Figure 2:
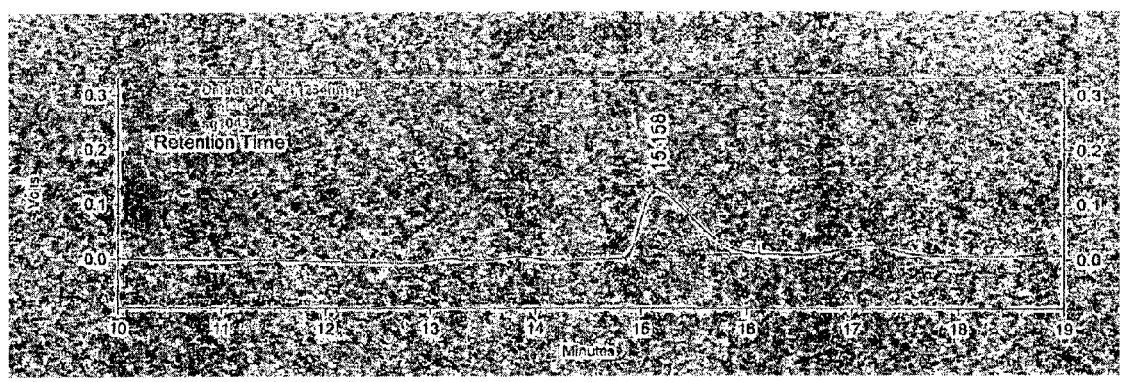
FIG. 2: Chromatogram for optically pure venlafaxine
FIG. 3 Scheme I indicates Retrosynthetic analysis of (−)-venlafaxine.
Figure 3:
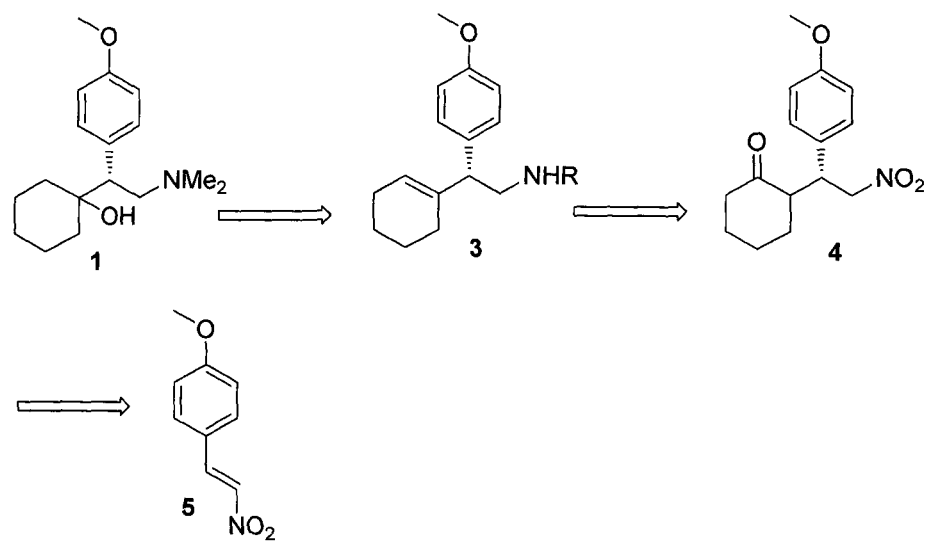
Figure 4:
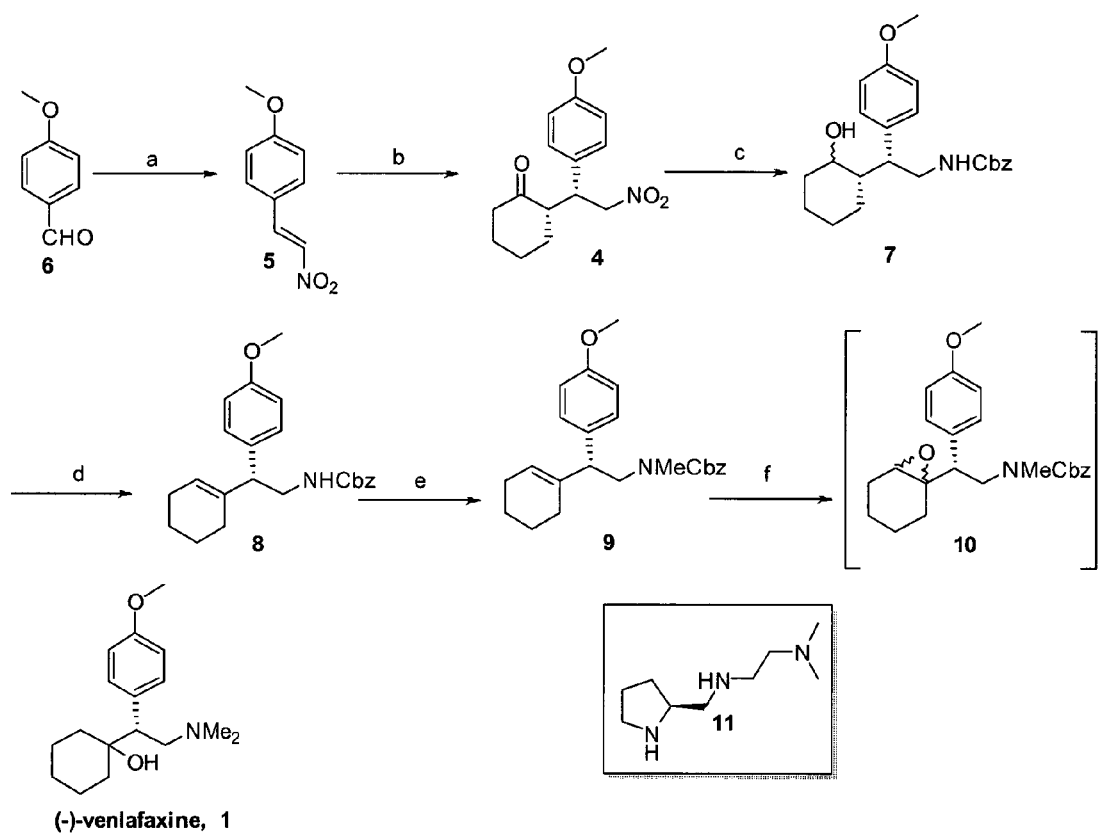
FIG. 4: Scheme 2 indicates synthesis of venlafaxine

Abbreviations used:
PTSA: para-Toluene sulphonic acid.

THF: Tetrahydrofuran.

Cbz: Carbobenzyloxy.

Ms: Methanesulphonyl

DBU: 1,8-Diazabicyclo[5.4.0]undec-7-ene.

m-CPBA: meta-Chloroperoxybenzoic acid.

DCM: Dichloromethane

LAH: Lithium aluminium hydride.

The process of the invention is outlined in Scheme 1.

According to retrosynthetic analysis, synthesis of (−)-venlafaxine began with Henry reaction of commercially cheap, easily available starting material anisaldehyde 6 with nitromethane in presence of ammonium acetate in acetic acid under sonication condition at room temperature to furnish nitro styrene 5 in 95% yield. Michael addition of nitro styrene 5 with cyclohexanone in presence of proline based organocatalyst 11 gives nitro keto compound 4 in 79% with ≥99% ee after stirring 24 hours at room temperature in presence of p-toluene sulphonic acid (PTSA) as an additive in DMF solvent. Selective reduction of keto 4 using $NaBH_4$ in $THF:H_2O$ (9:1) as solvent system afforded alcohol. The crude alcohol was subjected to nitro reduction by $NiCl_2.6H_2O$ and sodium borohydride in MeOH as a solvent, then the resultant amine was in situ protected by benzylchloroformate in presence $Et_3N$ as a base to furnish Cbz protected amino alcohol 7 in 75% yield.

Scheme 2. Reagents and conditions: a) Nitromethane, $NH_4OAc$, glacial acetic acid,))), 3 hrs, 95%; b) Cyclohexanone, 11, PTSA, DMF, 24 hrs, 79%, ≥99% ee; c) i) $NaBH_4$, $THF:H_2O$ (9:1), 2 hrs.; ii) $NiCl_2.6H_2O$, $NaBH_4$, MeOH, 1.5 hrs., 0° C. then CbzCl, $Et_3N$, rt, overnight, 75% (over two steps); d) i) MSCl, $Et_3N$, reflux, 14 hrs; ii) DBU, $CH_3CN$, 24 hrs, reflux, 68% (over two steps); e) MeI, NaH, THF, overnight, rt, 92%; f) i) m-CPBA, $NaHCO_3$, DCM, 2 hrs., rt. $LiAlH_4$, THF, 5 hrs, reflux, 60%, ≥99% ee.

The hydroxyl group of compound 7 was converted into corresponding mesyl derivative by using mesyl chloride in presence of $Et_3N$ as a base in DCM solvent under reflux condition. The crude mesylated reaction mixture on treatment with DBU in acetonitrile solvent furnished selectively more substituted double bond product 8 in 68% yield. After introduction of double bond dihydroxylation reaction condition was tried for installation of tertiary hydroxyl group. After successful installation of diol through dihydroxylation ($OSO_4$, NMO), selective removal of secondary hydroxyl group failed. So it was decided to install tertiary hydroxyl group through epoxidation and followed by epoxide opening. Thus the compound 8 was subjected with NaH and MeI in dry THF to afford compound 9 in 92% yield. For epoxidation compound 9 was treated with m-CPBA in presence of $NaHCO_3$ in DCM to afford epoxide. The crude epoxide 10 was subjected to selective epoxide opening as well as carbamate reduction in one pot using lithium aluminum hydride at reflux condition in THF to afford (−)-venlafaxine 1 in 60% yield with ≥99% ee. Spectral data and optical rotation for (−)-Venlafaxine 1 is provided herein in the form of examples.

This strategy of asymmetric synthesis of venlafaxine 1 by using organocatalyst can be extended to the synthesis of both enantiomers by switching the stereocentre of the catalyst with no loss in the optical activity of desired product. Derivatives of venlafaxine can be prepared in the same manner.

The invention is now explained with reference to embodiments and preferred embodiments, which in no way should be construed to be restrictive.

EXAMPLES

Example 1

Synthesis of (−)-Venlafaxine

Reacting anisaldehyde (20 gm, 0.147 mol) with nitromethane (94 mL, 1.741 mol) in presence of ammonium acetate in acetic acid (24 mL, 0.419 mol) under sonication condition at room temperature (25° C.) for a period of 3 hrs to furnish 24.7 gm nitro styrene 5 in 95% yield. Michael addition of nitro styrene 5 (3 gm, 16.8 mmol) with cyclohexanone (8.2 gm, 84 mmol) in presence of proline based organocatalyst (S)—N1,N1-dimethyl-N2-(pyrrolidin-2-ylmethyl)ethane-1,2-diamine (115 mg, 0.67 mmol) gives 6.1 gm of (S)-2-((R)-1-(4-methoxyphenyl)-2-nitroethyl)cyclohexan-1-one 4 in 79% with ≥99% ee after stirring 24 hours at room temperature (25° C.) in presence of pr-toluene sulphonic acid (PTSA) (127 mg, 0.67 mmol) as an additive in DMF solvent. Selective reduction of keto 4 (2 gm, 7.2 mmol) using $NaBH_4$ (0.816 gm, 21.6 mmol) in $THF:H_2O$ (9:1) (20 ml), as solvent system afforded (2.5)-2-((R)-1-(4-methoxyphenyl)-2-nitroethyl)cyclohexan-1-ol. The crude alcohol (2.06 gm, 7.4 mmol) was subjected to nitro reduction by $NiCl_2.6H_2O$ (4.4 gm, 18.5 mmol) and sodium borohydride (7.03 gm, 0.185 mol) in MeOH (20 mL) as a solvent, then the resultant amine was in situ protected by benzylchloroformate (3.7 ml, 22.2 mmol) in presence $Et_3N$ (4 mL, 29.6 mmol) as a base to furnish 2.07 gm Cbz protected amino alcohol benzyl ((2R)-2-((1S)-2-hydroxycyclohexyl)-2-(4-methoxyphenyl)carbamate in 75% yield. The hydroxyl group of Cbz protected amino alcohol (100 mg, 0.26 mmol) was converted into corresponding mesyl derivative by using mesyl chloride (0.06 mL, 0.78 mmol) in presence of $Et_3N$ (0.22 mL, 1.56 mmol) as a base in DCM solvent under reflux condition (40° C.) for 14 hrs The crude mesylated reaction mixture (120 mg) on treatment with DBU (1 mL) in acetonitrile solvent (3 mL) furnished 64.6 mg of selectively more substituted double bond product 8 benzyl (R)-(2-(cyclohex-1-en-1-yl)-2-(4-methoxyphenyl)ethyl)carbamate in 68% yield. After introduction of double bond dihydroxylation reaction condition was tried for installation of tertiary hydroxyl group.

After successful installation of diol through dihydroxylation ($OsO_4$, NMO), selective removal of secondary hydroxyl group failed. So it was decided to install tertiary hydroxyl group through epoxidation and followed by epoxide opening. Thus the compound 8 (100 Mg, 0.274 mmol) was subjected with NaH (22 mg, 0.55 mmol, 60%) and MeI (0.034 mL, 0.55 mmol) in dry THF (5 mL) to afford 95 mg compound 9 benzyl (R)-(2-(cyclohex-1-en-1-yl)-2-(4-methoxyphenyl)ethyl)(methyl)carbamate in 92% yield. To a cold (0° C.), magnetically stirred solution of N-methylCbz compound 9 (235 mg, 0.6 mmol) in distilled DCM (5 ml), $NaHCO_3$ (126 mg, 1.5 mmol) was added followed by 60% mCPBA (348 mg, 1.2 mmol) was added portion wise and stirred for 2 hrs at rt (25° C.) The reaction was quenched with solid $NaHCO_3$ (300 mg) and stirred for further 15 min. The reaction mixture was extracted with DCM (3×5 ml) and the combined organic layer was washed with brine (7 mL) and dried over anhydrous $Na_2SO_4$, filtered and concentrated under reduced pressure. The crude reaction mixture was used as such in the next reaction without further purification.

To a cold (0° C.), magnetically stirred solution of lithium aluminum hydride (100 mg, 2.5 mmol) in dry THF (5 ml), crude epoxide 10 (100 mg, 0.25 mmol) was added dropwise and refluxed (66° C.) for 5 hrs. The reaction mixture was cooled to 0° C. and excess LAH was quenched with ethyl acetate and then by addition of water, stirred for 2 hrs. Evaporation of the solvent furnished a residue which was extracted with ethyl acetate (3×20 mL). The combined organic layer was washed with brine (20 mL) and dried over anhydrous $Na_2SO_4$, filtered and concentrated under reduced pressure. Purification of the residue on a silica gel column using ethyl acetate as eluent furnished the (−)-venlafaxine 1 (103 mg, 60%) as a white solid.

Example 2

Characterization Data of (−)-Venlafaxine

The product of the process enlisted in example 1 was characterized by IR and $^1H$ and $^{13}C$ NMR and results are as follows:

$R_f$ (100% EtOAc) 0.2 (long tail); IR ($CHCl_3$): 3164, 2982, 2938, 2860, 2782, 1610, 1512 $cm^{-1}$;

$^1H$ NMR (200 MHz, $CDCl_3+CCL_4$): $^1H$ NMR (200 MHz, $CDCl_3+CCL_4$): 0.83-1.00 (m, 2H), 1.23-1.76 (m, 8H), 2.28 (dd, J=12.2, 2.9 Hz, 1H), 2.33 (s, 6H), 2.93 (dd, J=12.2, 2.9 Hz, 1H), 3.28 (t, J=12.2 Hz, 1H), 3.79 (s, 3H), 6.79 (d, J=8.8 Hz, 2H), 7.03 (d, j=8.79 Hz, 2H). $^{13}C$ NMR (50 MHz, $CDCl_3+CCL_4$): 20.70, 21.05, 25.55, 30.72, 37.53, 44.89, 51.20, 54.36, 60.74, 73.48, 112.75, 129.43, 132.00, 157.72.

Example 3

Optical Purity of (−)-Vanlafaxine (R)-venlafaxine [α]=−24.285 (c=1.04, EtOH).
Column: Kromasil 5-Amy Coat (250×4.6 mm)
Mobile Phase:EtOH:Pet ether: Diethylamine (05:95:0.5)
Wave length: 254 nm

| Racemic: Retention time Area % | Chiral Retention time Area % |
|---|---|
| 12.075 | 47.587 |
| 15.158 | 100.000 |
| 15.283 | 52.413 |

ADVANTAGES OF INVENTION

1. Use of cheap and easily available raw materials
2. Use of cheap and environmentally friendly catalyst
3. Avoidance of expensive and metal based catalyst
4. Avoidance of additional steps involving resolution of enantiomers
5. High % ee purity of product obtained

We claim:

1. A process for asymmetric synthesis of enantiomerically pure venlafaxine with ee≥99% comprising the steps of:
   a. reacting anisaldehyde with nitromethane in mole ratio 1:11.8 in presence of ammonium acetate in acetic acid under sonication condition at room temperature ranging between 25-35° C. for a period ranging between 2-4 hrs to obtain nitro styrene;
   b. michael addition of nitrostyrene as obtained in step (a) with cyclohexanone in mole ratio 1:5 in presence of proline based organocatalyst under stirring at room temperature ranging between 25-35° C. for a period ranging between 23-25 hrs in the presence of p-toluene sulphonic acid to obtain nitro ketone;
   c. reducing nitro ketone of step (b) using $NaBH_4$ in THF: H2O (9:1) to obtain crude alcohol (2S)-2-((R)-1-(4-methoxyphenyl)-2-nitroethyl)cyclohexan-1-ol which on subjecting to nitro reduction by $NiCl_2.6H_2O$ and sodium borohydride in MeOH as a solvent, afforded the resultant amine (2S)-2-((R)-2-amino-1-(4-methoxyphenyl)ethyl)cyclohexan-1-ol which on in situ protection by benzylchloroformate in presence of $Et_3N$ as a base furnished Cbz protected amino alcohol benzyl ((2R)-2-((1S)-2-hydroxycyclohexyl)-2-(4-methoxyphenyl)ethyl)carbamate;
   d. treating amino alcohol of step (c) with mesyl chloride in presence of $Et_3N$ as a base in DCM solvent under reflux condition at temperature ranging between 40-4° C. for a period ranging 14-25 hrs to give the crude mesylated reaction mixture which further on treatment with DBU in acetonitrile solvent furnished selectively more substituted double bond product benzyl (R)-(2-(cyclohex-1-en-1-yl)-2-(4-methoxyphenyl)ethyl)carbamate;
   e. subjecting compound (R)-2-(cyclohex-1-en-1-yl)-2-(4-methoxyphenyl)ethyl)carbamate of step (d) with NaH and MeI in dry THF to obtain benzyl (R)-(2-(cyclohex-1-en-1-yl)-2-(4-methoxyphenyl)ethyl)(methyl)carbamate;
   f. epoxidation of benzyl (R)-(2-(cyclohex-1-en-1-yl)-2-(4-methoxyphenyl)ethyl)(methyl)carbamate of step (e) by treating with m-CPBA in presence of $NaHCO_3$ in DCM under stirring at temperature ranging between 25-35° C. for a period ranging between 1-3 hrs to afford crude epoxide benzyl ((2R)-2-(7-oxabicyclo[4.1.0]heptan-1-yl)-2-(4-methoxyphenyl)ethyl)(methyl)carbamate;
   g. subjecting the crude epoxide of step (f) to selective epoxide opening as well as carbamate reduction in one pot using lithium aluminum hydride at reflux condition at temperature ranging between 65-70° C. for a period ranging 4-5 hrs in THF to afford (−)-venlafaxine.

2. The process according to claim 1, wherein the yield of enantiomerically pure (−)-venlafaxine is in the range of 21-58%.

3. The process according to claim 1, wherein the enantioselectivity of (−)-venlafaxine is in the range of 97-99%.

4. The process according to claim 1, wherein proline based organocatalyst used in step (b) is (S)—N1,N1-dimethyl-N2-(pyrrolidin-2-ylmethyl)ethane-1,2-diamine.

\* \* \* \* \*